US009895359B1

(12) United States Patent
Osborne

(10) Patent No.: US 9,895,359 B1
(45) Date of Patent: Feb. 20, 2018

(54) INHIBITION OF CRYSTAL GROWTH OF ROFLUMILAST

(71) Applicant: ARCUTIS, INC., Menlo Park, CA (US)

(72) Inventor: David W. Osborne, Fort Collins, CO (US)

(73) Assignee: ARCUTIS, INC., Menlo Park, CA (US)

( * ) Notice: Subject to any disclaimer, the term of this patent is extended or adjusted under 35 U.S.C. 154(b) by 0 days.

(21) Appl. No.: 15/616,409

(22) Filed: Jun. 7, 2017

(51) Int. Cl.
| | |
|---|---|
| *A61K 31/44* | (2006.01) |
| *A61K 47/10* | (2017.01) |
| *A61K 9/00* | (2006.01) |
| *A61K 9/14* | (2006.01) |
| *C09K 15/06* | (2006.01) |
| *A61K 45/06* | (2006.01) |

(52) U.S. Cl.
CPC ............ *A61K 31/44* (2013.01); *A61K 9/0014* (2013.01); *A61K 9/145* (2013.01); *A61K 45/06* (2013.01); *A61K 47/10* (2013.01); *C09K 15/06* (2013.01)

(58) Field of Classification Search
CPC ...... A61K 47/10; A61K 31/44; A61K 9/0014; A61K 9/145
See application file for complete search history.

(56) References Cited

U.S. PATENT DOCUMENTS

| | | | |
|---|---|---|---|
| 5,712,298 | A | 1/1998 | Amschler |
| 7,951,398 | B2 | 5/2011 | Dietrich et al. |
| 8,536,206 | B2 | 9/2013 | Kohl et al. |
| 9,205,044 | B2 | 12/2015 | Linder |
| 9,649,302 | B2 | 5/2017 | Vakkalanka |
| 2008/0280958 | A1 | 11/2008 | Bolle et al. |
| 2014/0303215 | A1 | 10/2014 | Bolle et al. |
| 2015/0099752 | A9 | 4/2015 | Bernal Anchuela et al. |
| 2015/0297601 | A1* | 10/2015 | Henkin .............. A61K 31/4375 424/489 |
| 2017/0152273 | A1* | 6/2017 | Merchant ............. A61K 9/0014 |

FOREIGN PATENT DOCUMENTS

| | | |
|---|---|---|
| EP | 1511516 A1 | 3/2005 |
| WO | 9501338 A1 | 1/1995 |
| WO | 2013030789 A1 | 3/2013 |
| WO | 2015132708 A1 | 9/2015 |

OTHER PUBLICATIONS

Snape et al., "A phase I randomized trial to assess the effect on skin infiltrate thickness and tolerability of topical phosphodiesterase inhibitors in the treatment of psoriasis vulgaris using a modified psoriasis plaque test", British Journal of Dermatology (2016) 175, pp. 479-486.
Pudipeddi et al., "Trends in Solubility of Polymorphs", Journal of Pharmaceutical Sciences, May 2005, vol. 94, Issue 5, pp. 929-939, Abstract only.
Patzelt et al., "Hair follicles, their disorders and their opportunities", Drug Discovery Today: Disease Mechanisms, vol. 5, Issue 2, Summer 2008, pp. e173-e-181.
Akhtar et al., "Exploring preclinical and clinical effectivenss of nanoformulations in the treatment of atopic dermatitis: Safety aspects and patent reviews", Bulletin of Faculty of Pharmacy, Cairo University 55 (2017), 1-10.
Karande et al., "Enhancement of transdermal drug delivery via synergistic action of chemicals", Biochimica ET Biophysica Acta, 1788 (2009), pp. 2632-2373.
Lorimer, "Thermodynamics of solubility in mixed solvent systems", Pure & Appl. Chem 1993, vol. 65, 2, pp. 183-191.
Minghetti et al., "Ex Vivo Study of Transdermal Permeation of Four Diclofenac Salts from Different Vehicles", Journal of Pharmaceutical Sciences, vo. 96, No. 4, Apr. 2007, pp. 814-823.
Nair et al., "Basic considerations in the dermatokinetics of topical formulations", Brazilian Journal of Pharmaceutical Sciences, vol. 43, No. 3, Jul./Sep. 2013, pp. 423-434.
Osborne, "Diethylene glycol monoethyl ether: an emerging solvent in topical dermatology products", J. Cosmet Dermatol, Dec. 2011, 10(4), pp. 324-329, Abstract.
Pathan et al., "Chemical Penetration Enhancers for Transdermal Drug Delivery Systsms", Tropical Journal of Pharmaceutical Research, Apr. 2009, 8(2), pp. 173-179.
Sikarra et al., "Techniques for Solubility Enhancement of Poorly Soluble Drugs: An Overview", Journal of Medical Pharmaceutical and Allied Sciences, (2012), 01; pp. 1-22.
Tradename (roflumilast) Tablets NDA 22-522, Summary of Basis for the Recommended Action from Chemistry, Manufacturing, and Controls, Forest Research Institute, Inc., Reference ID 2901509, 3 pages.

* cited by examiner

*Primary Examiner* — Theodore R. West
(74) *Attorney, Agent, or Firm* — Rothwell, Figg, Ernst & Manbeck, P.C.

(57) ABSTRACT

Roflumilast crystals have been shown to increase in size during storage. The size of the roflumilast crystals can affect the bioavailability and efficacy of a pharmaceutical composition. The growth of roflumilast crystals can be inhibited during storage by including hexylene glycol in the composition. The resulting composition has improved bioavailability and efficacy and can be used to inhibit phosphodiesterase 4 in patient in need of such treatment.

16 Claims, 12 Drawing Sheets
(12 of 12 Drawing Sheet(s) Filed in Color)

INHIBITION OF CRYSTAL GROWTH OF ROFLUMILAST

FIELD OF THE INVENTION

The invention pertains to the inhibition of crystal growth or increased particle size upon storage of roflumilast that is suspended or has precipitated from a pharmaceutical product. More particularly, the invention pertains to a pharmaceutically acceptable emulsion, suspension, gel or solution formulated to inhibit suspended or precipitated roflumilast particles from changing in particle size distribution over time.

BACKGROUND OF INVENTION

Roflumilast is known to be suitable as a bronchial therapeutic agent as well as for the treatment of inflammatory disorders. Compositions containing roflumilast are used in human and veterinary medicine and have been proposed for the treatment and prophylaxis of diseases including but not limited to: inflammatory and allergen-induced airway disorders (e.g. bronchitis, asthma, COPD); dermatoses (e.g. proliferative, inflammatory and allergen induced skin disorders), and generalized inflammations in the gastrointestinal region (Crohn's disease and ulcerative colitis).

Roflumilast and its synthesis were described in U.S. Pat. No. 5,712,298 (the "'298 patent"), incorporated herein by reference.* It has long been recognized that pharmaceutical compounds having phosphodiesterase (PDE)-inhibiting properties, such as roflumilast, are useful for treating psoriasis and atopic dermatitis ('298 patent, col 11 lines 52-61) and other chronic inflammatory and allergen-induced dermatoses. For treatment of such dermatoses, roflumilast emulsions, suspensions, gels or solutions for topical application have been described ('298 patent, col 12, lines 37-64). Although oral tablets of roflumilast have been commercialized, the low aqueous solubility of the compound has been reported to be only 0.53 mg/l at 21° C. in WO95/01338 (corresponding to the '298 patent and incorporated herein by reference in its entirety). This low aqueous solubility has been problematic for the development of parenteral preparations and topical emulsions, suspensions, gels or solutions containing water. In U.S. Pat. No. 9,205,044 (incorporated herein by reference), the poor water solubility of roflumilast was overcome by using an alkoxylated fat, specifically polyoxyethylated 12-hydroxystearic acid, as a co-solvent for parenteral administration. In EP 151151681 (corresponding to published U.S. application Ser. No. 14/075,035 incorporated herein by reference), the low water solubility of roflumilast was overcome in topical emulsion (cream) formulations by formulating with polyethylene glycol 400 (PEG 400) in concentrations over 62% (w/w) while keeping water weight percentages under 10%.

* Unless otherwise indicated, references incorporated herein by reference are incorporated in their entireties for all purposes.

Topical application of potent pharmacological agents like roflumilast for treating skin diseases has been found to provide superior delivery, lower systemic exposure and greater ease of use for patients. The molecular structure of the compound ultimately dictates the ability of the drug to cross the epithelium of the tissue to which the product is applied. For topical application to skin, selection of the components of the formulation dictates the maximum skin permeation that the formulator can achieve. Creams, lotions, gels, ointments and foams are just a few of the more familiar forms of topical products that contain active pharmaceutical ingredients (API) for application to the skin. To assure consistent delivery of the API into or across the skin, it must remain either: 1) dissolved over the shelf life of the topical product, or 2) suspended as particles having unchanged crystal habit and unchanged particle size distribution over the shelf life of the topical product.

The ability of a dissolved active ingredient to permeate the barrier of the skin is determined by its molecular structure. A well-known relationship between molecular structure and skin penetration is that increasing molecular weight decreases the rate that an active crosses the skin (J D Bos, M M Meinardi, Exp Dermatol. 2000 June; 9(3):165-9). Another well-understood relationship is that increasing the octanol-water partition coefficient of a hydrophilic active initially increases the rate that an active permeates the skin, but then decreases skin permeation once the active becomes too lipophilic to partition out of the stratum corneum and into the lower layers of the epidermis (D. W. Osborne and W. J. Lambert, Prodrugs for Dermal Delivery, K. B. Sloane ed., Marcel Dekker, New York 163-178 (1992)). The optimal octanol-water partition coefficient is usually at log P values of 2-3. The rate that an active ingredient crosses into the viable epidermis can be further modified based on the composition of the topical product. Final pH of the formulation may be critical, because dissolved ionized active ingredients typically do not permeate the skin as effectively as active ingredients that do not carry a charge (N. Li, X. Wu, W. Jia, M. C. Zhang, F. Tan, and J Zhang. *Drug Dev Indust Pharm* 38(8)985-994). Functional ingredients such as skin penetration enhancers (D. W. Osborne and J. J. Henke, Pharmaceutical Technology 21(11)58-66(1997)) can be added to the topical product to increase skin permeation. For a dissolved active in the topical product, the closer the drug concentration is to the amount of active required to saturate the drug product, the greater the thermodynamic driving force of the active to cross the skin, i.e. the greater the skin flux of the active. The scientific literature guides formulators on how to increase penetration through the polar route, the nonpolar route, and the intercellular lipid pathway or transfollicular penetration. While these theories and mechanisms are sometimes conflicting, it is generally accepted that the most consistent skin permeation of a drug from a topical product occurs when the active ingredient is dissolved in the formulation. For this reason, formulators generally avoid developing a topical product that will have particles or crystals of the active ingredient precipitate during storage according to labeled storage instructions. Precipitation of the active ingredient can occur for various reasons. Particular active ingredients, when formulated with particular pharmaceutical excipients will tend to form supersaturated solutions. At the time of manufacture, all of the active ingredient will be in solution. After days, weeks, or months, this metastable topical product will equilibrate and active ingredient particles will form. If a topical product contains a volatile solvent such as ethanol, then evaporation of the solvent upon storage could result in precipitation of the active ingredient. A less soluble polymorph (Pudipeddi and Serajuddin, J. Pharm. Sci., 94(5) 929-939 (2005)) may nucleate in the topical product and form active ingredient particles that will not re-dissolve. Other products may be formulated too close to the saturation limit of the active ingredient with the result that minor shifts in storage temperatures will cause precipitation. It should be noted that the dramatic temperature shifts that can occur during shipping are expected to cause the reversible precipitation of the active ingredient. Regardless of the reason, irreversible precipitation of the active ingredient during storage of a topical product can have profound effects on the bioavailability and efficacy of a topical product, since only dissolved active ingredients can penetrate into intact stratum corneum, the outermost layer of epithelium of the skin.

For a suspended active ingredient, properties in addition to molecular structure influence skin permeation. The ratio of dissolved to suspended active ingredient can have a significant influence on the amount of active delivered after topical application. It has been shown that optimal drug delivery can be achieved for particular drugs and particular diseases by utilizing a topical composition that includes a dissolved active ingredient that has the capacity to permeate the stratum corneum layer of the epidermis and become available systemically, along with an active ingredient in a microparticulate state that does not readily cross the stratum corneum of the epidermis (U.S. Pat. No. 5,863,560 hereby incorporated by reference). Another property of a suspended active ingredient that affects its delivery is the distribution of suspended particle size. It has been shown that a 6 micron particle will target the hair follicle and penetrate to a depth of 500 micrometers in a terminal hair. For a suspended particle of 0.75 microns to 1.5 microns in size, the particle penetrates the terminal hair shaft to a depth of 800 micrometers (A Patzelt, F Knorr, U Blume-Peytavi, W Sterry, J Lademann, Drug Discovery Today: Disease Mechanisms, 5(2)2008 pages e173-e181). Thus, for suspended active ingredients, skin permeability depends on the following properties: 1) molecular structure of dissolved active ingredient, 2) particulate/crystalline structure of the suspended active ingredient, 3) particle size of the suspended active ingredient, and 4) particle size distribution of the suspended active ingredient. The ability of a topical product composition to modify the skin permeation is similar for suspended active ingredients and dissolved active ingredients. Because skin permeability is dependent upon additional properties of the suspended active ingredients, consistent delivery from topical products containing suspended actives is more difficult to maintain than for topical products containing only dissolved active ingredients.

Consistent delivery of a suspended active ingredient from a topical product is assured by formulation into a product in which the suspended particles do not significantly change in size or amount over the shelf life of the product. Change over time in the ratio of dissolved active ingredient to particulate active ingredient can dramatically change the skin permeation of the active ingredient. The same mechanisms described above (supersaturation, temperature changes, evaporation, polymorphic transformation) that can cause precipitation of dissolved active ingredients can alter the dissolved-to-particulate ratio for suspended active ingredients. Change over time in the particle size or particle size distribution of the dispersed active ingredient can also dramatically change the skin permeation of the active ingredient. Sometimes this change in particle size or particle size distribution can be explained by Ostwald ripening of the particles. Ostwald ripening occurs when small particles in the topical product dissolve and redeposit onto larger particles suspended in the same container of topical product. Over time this phenomenon shifts the particle size distribution toward larger particles at the expense of the smaller particles. Ostwald ripening and precipitation of a less soluble polymorph are two major problems in developing topical products containing suspended actives.

A need exists for a non-irritating and non-sensitizing additive that can be safely added to a topical roflumilast product to prevent change in the size of suspended active ingredient particles. Such an additive would be useful in any roflumilast composition which is likely to experience crystal growth or an increase in particle size during storage. Crystal growth and changes in particle size also can affect the administration and/or bioavailability of roflumilast pharmaceutical formulations other than topical formulations, such as parenteral and pulmonary formulations.

SUMMARY OF THE INVENTION

In accordance with the present invention, it has been discovered that hexylene glycol inhibits crystalline growth of suspended or precipitated roflumilast particles in formulations containing pharmaceutically acceptable solvents including water. Inhibiting crystalline growth of suspended or precipitated roflumilast particles is particularly important in topically applied formulations due to skin permeability.

BRIEF DESCRIPTION OF THE DRAWINGS

The patent or application file contains at least one figure executed in color. Copies of this patent or patent application publication with color figures will be provided by the Office upon request and payment of the necessary fee.

FIG. 11a shows Sample 36-1 roflumilast particles precipitated in a cream composition with diethylene glycol monoethyl ether (DEGEE) and without hexylene glycol. The three largest roflumilast particles were measured (0.07 mm×0.09 mm; 0.06 mm×0.06 mm; and 0.10 mm×0.05 mm) and found to have a mean surface area of 5,000 square microns. FIG. 11b shows Sample 36-2 roflumilast particles precipitated in a cream composition with both diethylene glycol monoethyl ether (DEGEE) and hexylene glycol. The three largest roflumilast particles were measured (0.05 mm×0.03 mm; 0.05 mm×0.03 mm and 0.05 mm×0.03 mm) and found to have a mean surface area of 1,500 square microns.

DETAILED DESCRIPTION OF THE INVENTION

Figure 1:
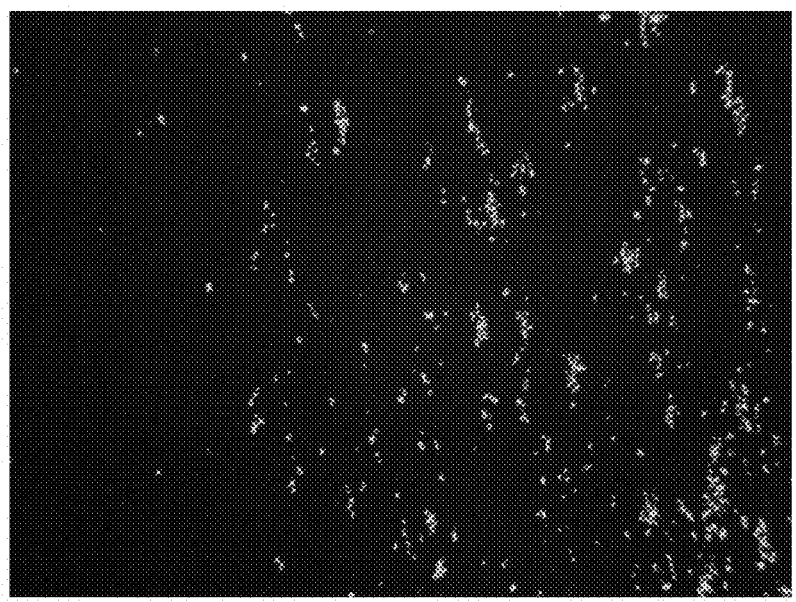
FIG. 1 shows Sample 19-2 "dry" roflumilast crystals from ferrer-Interquim S.A. Batch A14367P, the drug substance used in all the examples in this specification. The roflumilast crystals are 0.01 mm-0.02 mm in length.

Roflumilast is a compound of the formula (I)

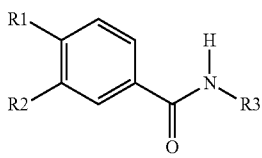

wherein R1 is difluoromethoxy, R2 is cyclopropylmethoxy and R3 is 3,5-dichloropyrid-4-yl.

This compound has the chemical name N-(3,5-dichloropyrid-4-yl)-3-cyclopropylmethoxy-4-difluoromethoxybenzamid-e (INN: roflumilast).

Hexylene glycol (PharmaGrade. USP/NF) is 2-methyl-2,4-pentanediol of the formula (II).

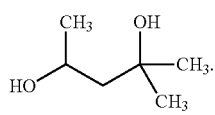

The present invention is directed to the addition of hexylene glycol to a roflumilast-containing pharmaceutical composition that contains a pharmaceutically acceptable solvent, including water, to inhibit growth of roflumilast crystals in the composition. For topical products designed to contain suspended roflumilast particles or crystals, the addition of hexylene glycol to a composition containing roflumilast, will inhibit (i.e., prevent or substantially reduce in comparison to compositions that do not contain a hexylene glycol) changes in particle size distribution over the shelf life of the product and assure consistent bioavailability. For topical products designed to have roflumilast completely dissolved, hexylene glycol inhibits the growth of precipitated roflumilast particles.

Drug products that have fully dissolved drug substance for the labeled storage conditions over product shelf life will have the active precipitate if the product is formulated to maintain significant thermodynamic driving force. Typical storage conditions for a topical pharmaceutical cream are: Store at room temperature: 60° F./15° C.–80° F./26° C. Do not freeze. It is understood by product development scientists and regulatory agency reviewers that a topical product will not always be stored over this temperature range. Therefore, the FDA requires that all topical products undergo freeze-thaw cycling and temperature excursion studies. The active is neither required nor expected to remain in solution when the product is exposed to temperatures of −20° C., dramatically below 15° C. (60° F.) of the labeled storage condition. Since topical products containing completely dissolved drug are usually formulated near saturation, i.e. near maximum thermodynamic driving force, most topical products experience precipitation of the active ingredient during freeze-thaw cycling or temperature excursion studies. The addition of hexylene glycol prevents crystal growth of roflumilast when precipitation occurs due to temperature excursions below the labeled storage conditions. Inhibiting crystal growth assures that any precipitated active will quickly return to being completely dissolved once the product is returned to controlled room temperature. The prompt return of the precipitated roflumilast to a fully dissolved state assures consistent, reproducible bioavailability, efficacy and safety of the topically applied product. Hexylene glycol can be added between 0.1% and 20% on a weight/weight basis, preferably between 0.25% and 8% on a weight/weight basis and most preferably between 0.5% and 2% on a weight/weight basis.

The topical roflumilast product formulations that benefit from the addition of hexylene glycol include but are not limited to aerosols, foams, sprays, emulsions (which can also be called creams, lotions, or ointments), gels (two phase or single phase), liquids, ointments, pastes, shampoos, suspensions, and systems. These are the tier two terms within compendia taxonomy for dosage forms containing pharmaceutical active ingredients (US Pharmacopeia <1151>).

The roflumilast formulations can be prepared by methods known in the art (e.g. see the '298 patent and U.S. application Ser. No. 14/075,035).

Preferably, hexylene glycol is added to compositions containing 0.005-2.0% roflumilast that may be in one of the following forms:

An oil-in-water emulsion: The product may be formulations in which hexylene glycol is added to an emulsion comprising a discrete phase of a hydrophobic component and a continuous aqueous phase that includes water and optionally one or more polar hydrophilic excipients as well as solvents, co-solvents, salts, surfactants, emulsifiers, and other components. These emulsions may include water-soluble or water-swellable polymers that help to stabilize the emulsion.

Thickened Aqueous gels: These systems include an aqueous phase which has been thickened by suitable natural, modified natural, or synthetic thickeners such as described below. Alternatively, the thickened aqueous gels can be thickened using suitable polyethoxylate alky chain surfactants or other nonionic, cationic, or anionic systems.

Thickened Hydroalcoholic gels: These systems include a blend of water and alcohol as the polar phase which has been thickened by suitable natural, modified natural, or synthetic polymers such as described below. Alternatively, the thickened hydroalcoholic gels can be thickened using suitable polyethoxylate alky chain surfactants or other nonionic, cationic, or anionic systems. The alcohol can be ethanol, isopropyl alcohol or other pharmaceutically acceptable alcohol.

Hydrophilic gels: These are systems in which the continuous phase includes at least one water soluble or water dispersible hydrophilic component other than water. The formulations may optionally also contain water up to 60% by weight. Higher levels may be suitable in some compositions. Suitable hydrophilic components include one or more glycols such as polyols such as glycerin, propylene glycol, butylene glycols, polyethylene glycols (PEG), random or block copolymers of ethylene oxide, propylene oxide, and/or butylene oxide, polyalkoxylated surfactants having one or more hydrophobic moieties per molecule, silicone copolyols, blend of ceteareth-6 and stearyl alcohol as well as combinations thereof, and the like.

A water-in-oil emulsion: The compositions may be formulations in which roflumilast is incorporated into an emulsion that includes a continuous phase of a hydrophobic component and an aqueous phase that includes water and optionally one or more polar hydrophilic carrier(s) as well as salts or other components. These emulsions may include oil-soluble or oil-swellable polymers as well as one or more emulsifier(s) that help to stabilize the emulsion.

A hydrophilic or hydrophobic ointment: The compositions are formulated with a hydrophobic base (e.g. petrolatum, thickened or gelled water insoluble oils, and the like) and optionally having a minor amount of a water soluble phase. Hydrophilic ointments generally contain one or more surfactants or wetting agents Solvents Compositions according to the present invention may include one or more solvents or co-solvents to obtain the desired level of active ingredient solubility in the topical product. The solvent may also modify skin permeation or the activity of other excipients contained in the formulation. Solvents include but are not limited to acetone, ethanol, benzyl alcohol, butyl alcohol, diethyl sebacate, diethylene glycol monoethyl ether, diisopropyl adipate, dimethyl sulfoxide, ethyl acetate, isopropyl alcohol, isopropyl isostearate, isopropyl myristate, N-methyl pyrrolidinone, polyethylene glycol, glycerol, propylene glycol and SD alcohol.

Moisturizers

Compositions according to the present invention may include a moisturizer to increase the level of hydration. The moisturizer can be a hydrophilic material including humectants or it can be a hydrophobic material including emollients. Suitable moisturizers include but are not limited to: 1,2,6-hexanetriol, 2-ethyl-1,6-hexanediol, butylene glycol, glycerin, polyethylene glycol 200-8000, butyl stearate, cetostearyl alcohol, cetyl alcohol, cetyl esters wax, cetyl palmitate, cocoa butter, coconut oil, cyclomethicone, dimethicone, docosanol, ethylhexyl hydroxystearate, fatty acids, glyceryl isostearate, glyceryl laurate, glyceryl monostearate, glyceryl oleate, glyceryl palmitate, glycol distearate, glycol stearate, isostearic acid, isostearyl alcohol, lanolin, mineral oil, limonene, medium-chain triglycerides, menthol, myristyl alcohol, octyldodecanol, oleic acid, oleyl alcohol, oleyl oleate, olive oil, paraffin, peanut oil, petrolatum, Plastibase-50W, and stearyl alcohol.

Surfactants and Emulsifiers

Compositions according to the present invention optionally can include one or more surfactants to emulsify the composition and to help wet the surface of the actives or excipients. As used herein the term "surfactant" means an amphiphile (a molecule possessing both polar and nonpolar regions which are covalently bound) capable of reducing the surface tension of water and/or the interfacial tension between water and an immisicible liquid. Surfactants include but are not limited to alkyl aryl sodium sulfonate, Amerchol-CAB, ammonium lauryl sulfate, apricot kernel oil PEG-6 esters, Arlacel, benzalkonium chloride, Ceteareth-6, Ceteareth-12, Ceteareth-15, Ceteareth-30, cetearyl alcohol/ ceteareth-20, cetearyl ethylhexanoate, ceteth-10, ceteth-2, ceteth-20, ceteth-23, choleth-24, cocamide ether sulfate, cocamine oxide, coco betaine, coco diethanolamide, coco monoethanolamide, coco-caprylate/caprate, disodium cocoamphodiacetate, disodium laureth sulfosuccinate, disodium lauryl sulfoacetate, disodium lauryl sulfosuccinate, disodium oleamido monoethanolamine sulfosuccinate, docusate sodium, laureth-2, laureth-23, laureth-4, lauric diethanolamide, lecithin, mehoxy PEG-16, methyl gluceth-10, methyl gluceth-20, methyl glucose sesquistearate, oleth-2, oleth-20, PEG 6-32 stearate, PEG-100 stearate, PEG-12 glyceryl laurate, PEG-120 methyl glucose dioleate, PEG-15 cocamine, PEG-150 distearate, PEG-2 stearate, PEG-20 methyl glucose sesqustearate, PEG-22 methyl ether, PEG-25 propylene glycol stearate, PEG-4 dilaurate, PEG-4 laurate, PEG-45/dodecyl glycol copolymer, PEG-5 oleate, PEG-50 Stearate, PEG-54 hydrogenated castor oil, PEG-6 isostearate, PEG-60 hydrogenated castor oil, PEG-7 methyl ether, PEG-75 lanolin, PEG-8 laurate, PEG-8 stearate, Pegoxol 7 stearate, pentaerythritol cocoate, poloxamer 124, poloxamer 181, poloxamer 182, poloxamer 188, poloxamer 237 poloxamer 407, polyglyceryl-3 oleate, polyoxyethylene alcohols, polyoxyethylene fatty acid esters, polyoxyl 20 cetostearyl ether, polyoxyl 40 hydrogenated castor oil, polyoxyl 40 stearate, polyoxyl 6 and polyoxyl 32, polyoxyl glyceryl stearate, polyoxyl stearate, polysorbate 20, polysorbate 40, polysorbate 60, polysorbate 65, polysorbate 80, PPG-26 oleate, PROMULGEN™ 12, propylene glycol diacetate, propylene glycol dicaprylate, propylene glycol monostearate, sodium xylene sulfonate, sorbitan monooleate, sorbitan monopalmitate, sorbitan monostearate, steareth-2, steareth-20, steareth-21, steareth-40, tallow glycerides, and emulsifying wax.

Polymers and Thickeners

For certain applications, it may be desirable to formulate a product that is thickened with soluble, swellable, or insoluble organic polymeric thickeners such as natural and synthetic polymers or inorganic thickeners such as acrylates copolymer, carbomer 1382, carbomer copolymer type B, carbomer homopolymer type A, carbomer homopolymer type B, carbomer homopolymer type C, carboxy vinyl copolymer, carboxymethylcellulose, carboxypolymethylene, carrageenan, guar gum, hydroxyethyl cellulose, hydroxypropyl cellulose, microcrystalline wax, and methylcellulose, Additional Components Compositions according to the present invention may be formulated with additional components such as fillers, carriers and excipients conventionally found in cosmetic and pharmaceutical topical products. Additional components including but not limited to antifoaming agents, preservatives (e.g. p-hydroxybenzoic esters, benzyl alcohol, phenylmercury salts, chlorocresol), antioxidants, sequestering agents, stabilizers, buffers, pH adjusting solutions, skin penetration enhancers, film formers, dyes, pigments, diluents, bulking agents, fragrances and other excipients to improve the stability or aesthetics, may be added to the composition.

Compositions according to the present invention may be formulated with additional active agents depending on the condition being treated. The additional active agents include but are not limited to Anthralin (dithranol), Azathioprine, Tacrolimus, Coal tar, Methotrexate, Methoxsalen, Salicylic acid, Ammonium lactate, Urea, Hydroxyurea, 5-fluorouracil, Propylthouracil, 6-thioguanine, Sulfasalazine, Mycophenolate mofetil, Fumaric acid esters, Corticosteroids (e.g. Aclometasone, Amcinonide, Betamethasone, Clobetasol, Clocotolone, Mometasone, Triamcinolone, Fluocinolone, Fluocinonide, Flurandrenolide, Diflorasone, Desonide, Desoximetasone, Dexamethasone, Halcinonide, Halobetasol, Hydrocortisone, Methylprednisolone, Prednicarbate, Prednisone), Corticotropin, Vitamin D analogues (e.g. calcipotriene, calcitriol), Acitretin, Tazarotene, Cyclosporine, Resorcinol, Colchicine, Adalimumab, Ustekinumab, Infliximab, bronchodialators (e.g. beta-agonists, anticholinergics, theophylline), and antibiotics (e.g. erythromycin, ciprofloxacin, metronidazole).

Administration and Dosage

The compositions according to the present invention can be administered by any suitable administration route including but not limited to oral, rectal, parenteral (e.g. intradermal, subcutaneous, intramuscular, intravenous, intramedullary, intra arterial, intrathecal, epidural), ocular, inhalation, nebulization, cutaneously (topically), transdermally, and mucosally (e.g. sublingual, buccal, nasally). In a preferred embodiment, the composition is administered topically.

Suitable pharmaceutical dosage forms include but are not limited to emulsions, suspensions, sprays, oils, ointments, fatty ointments, creams, pastes, gels, foams transdermal patches and solutions (e.g. injectable, oral).

The composition preferably contains roflumilast, salts of roflumilast, the N-oxide of roflumilast or salts thereof in an amount of 0.005-2% w/w, more preferably 0.05-1% w/w, and most preferably 0.1-0.5% w/w per dosage unit.

The composition preferably contains hexylene glycol in an amount of between 0.1% and 20% w/w, more preferably between 0.25% and 8% w/w and most preferably between 0.5% and 2% w/w.

The composition can be administered one or more times per day, preferably the composition is administered 1-2 times per day.

The composition can be used in veterinary and in human medicine for the treatment and prevention of all diseases regarded as treatable or preventable by using roflumilast, including but not limited to acute and chronic airway disorders; proliferative, inflammatory and allergic dermatoses; disorders which are based on an excessive release of TNF and leukotrienes; disorders of the heart which can be treated by PDE inhibitors; inflammations in the gastrointestinal system or central nervous system; disorders of the eye; arthritic disorders; and disorders which can be treated by the tissue-relaxant action of PDE inhibitors. Preferably, the composition is used to treat proliferative, inflammatory and allergic dermatoses such as psoriasis (vulgaris), eczema, acne, Lichen simplex, sunburn, pruritus, alopecia areata, hypertrophic scars, discoid lupus erythematosus, and pyodermias.

The composition can include additional active agents suitable for treating the patient's condition. For example, when proliferative, inflammatory and allergic dermatoses are treated, the composition may additionally include Anthralin (dithranol), Azathioprine, Tacrolimus, Coal tar, Methotrexate, Methoxsalen, Salicylic acid, Ammonium lactate, Urea, Hydroxyurea, 5-fluorouracil, Propylthouracil, 6-thioguanine, Sulfasalazine, Mycophenolate mofetil, Fumaric acid esters, Corticosteroids (e.g. Aclometasone, Amcinonide, Betamethasone, Clobetasol, Clocotolone, Mometasone, Triamcinolone, Fluocinolone, Fluocinonide, Flurandrenolide, Diflorasone, Desonide, Desoximetasone, Dexamethasone, Halcinonide, Halobetasol, Hydrocortisone, Methylprednisolone, Prednicarbate, Prednisone), Corticotropin, Vitamin D analogues (e.g. calcipotriene, calcitriol), Acitretin, Tazarotene, Cyclosporine, Resorcinol, Colchicine, Adalimumab, Ustekinumab, Infliximab, and/or antibiotics.

The following examples are provided to enable those of ordinary skill in the art to make and use the methods and compositions of the invention. These examples are not intended to limit the scope of what the inventor regards as the invention. Additional advantages and modifications will be readily apparent to those skilled in the art.

Example 1

A few mg of roflumilast API (Batch A14367P from Interquim S.A.) dry powder was tapped onto a microscope slide, a coverslip was moved into place and crystal habit and particle size of the API was examined using polarized light microscopy using a 10× objective (FIG. 1, microscope sample 19-2).

Figure 2:
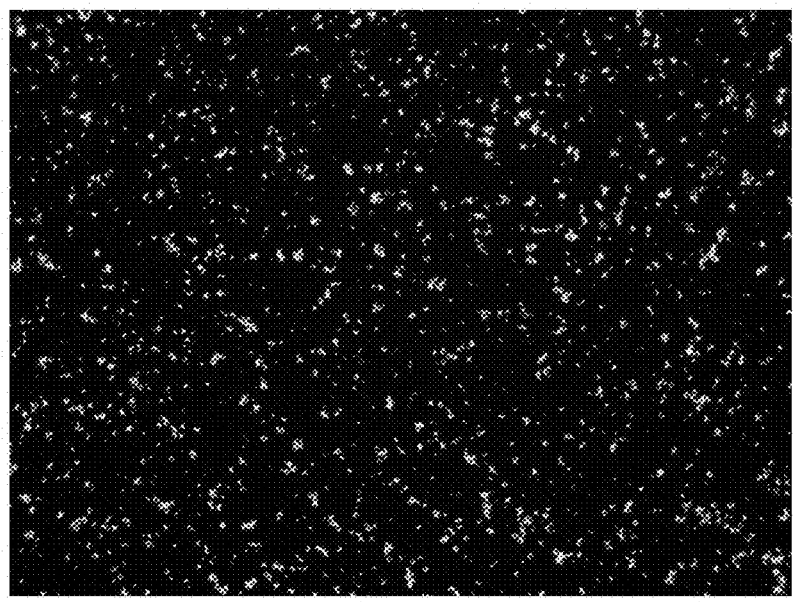
FIG. 2 shows Sample 20-3 roflumilast crystals suspended in equimolar hexylene glycol:water solution after storage for six weeks at room temperature under 10× power. The roflumilast crystals are 0.01 mm-0.02 mm in length.

0.0092 grams of roflumilast (Batch A14367P from Interquim S.A.) was weighed into a liquid scintillation vial. An equimolar blend of hexylene glycol (lot 1AC0818, Spectrum) and distilled water was added dropwise with mixing to the vial containing roflumilast to produce a suspension of roflumilast in excess of the solubility limit. An equimolar blend is 86.7% hexylene glycol and 13.3% water on a weight/weight percent basis. After mixing each addition of hexylene glycol:water blend, the tightly capped vial was returned to a water bath set at 25° C. It required 0.7962 grams of equimolar Hexylene Glycol:Water blend to completely dissolve the 0.0092 grams of roflumilast and give a 1.14% roflumilast in equimolar Hexylene Glycol:Water (wt/wt %) solution. 0.0064 grams of roflumilast was added to this sample (labeled 12-3) to form a finely dispersed suspension at 25° C. and the vial was then stored undisturbed at about 15-18° C., protected from the light for six weeks. A sample of the roflumilast crystals was removed from the vial, placed on a microscope slide (with coverslip) and then examined using polarized light microscopy using a 10× objective (FIG. 2, microscope sample 20-3).

Figure 3:
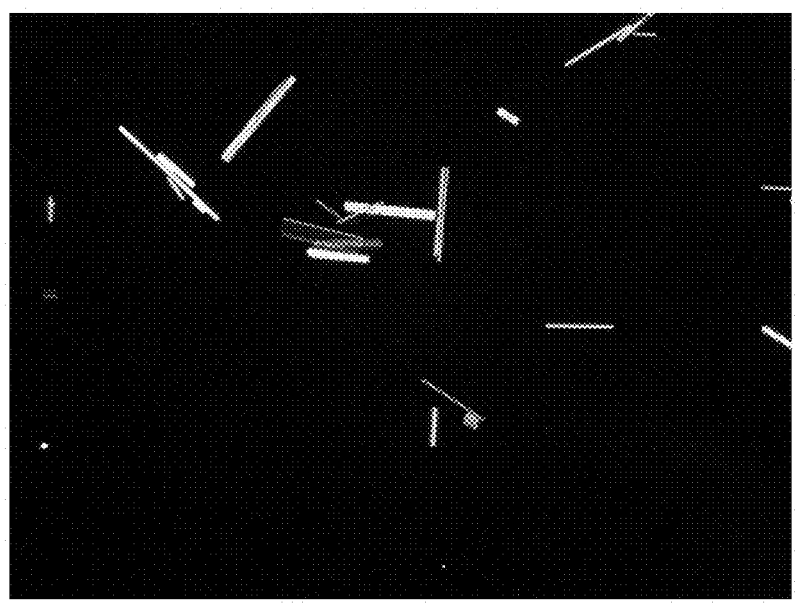
FIG. 3 shows Sample 20-2 roflumilast crystals suspended in equimolar diethylene glycol monoethyl ether:water solution after storage for six weeks at room temperature. The roflumilast crystals are 0.04 mm-0.20 mm in length and 0.01 mm-0.02 mm in width.

0.0111 grams of roflumilast (Batch A14367P from Interquim S.A.) was weighed into a liquid scintillation vial. An equimolar blend of diethylene glycol (DEGEE) (Transcutol P, lot 146063, Gattefosse) and distilled water was added dropwise with mixing to the vial containing roflumilast to produce a suspension of roflumilast in excess of the solubility limit. An equimolar blend is 88.3% DEGEE and 11.7% water on a weight/weight percent basis. After mixing each addition of DEGEE:water blend, the tightly capped vial was returned to a water bath set at 25° C. It required 0.2477 grams of equimolar DEGEE:Water blend to completely dissolve the 0.0111 grams of roflumilast and give a 4.29% roflumilast in equimolar DEGEE:Water (wt/wt %) solution. This sample (labeled 13-1) was a solution of roflumilast at 25° C. and the vial was then stored undisturbed at about 15-18° C., protected from the light for six weeks. Roflumilast crystals precipitated due to the cooler storage temperature. A sample of the roflumilast crystals was removed from the vial, placed on a microscope slide (with coverslip) and then examined using polarized light microscopy using a 10× objective (FIG. 3, microscope sample 20-2).

Example 2

Figure 4:
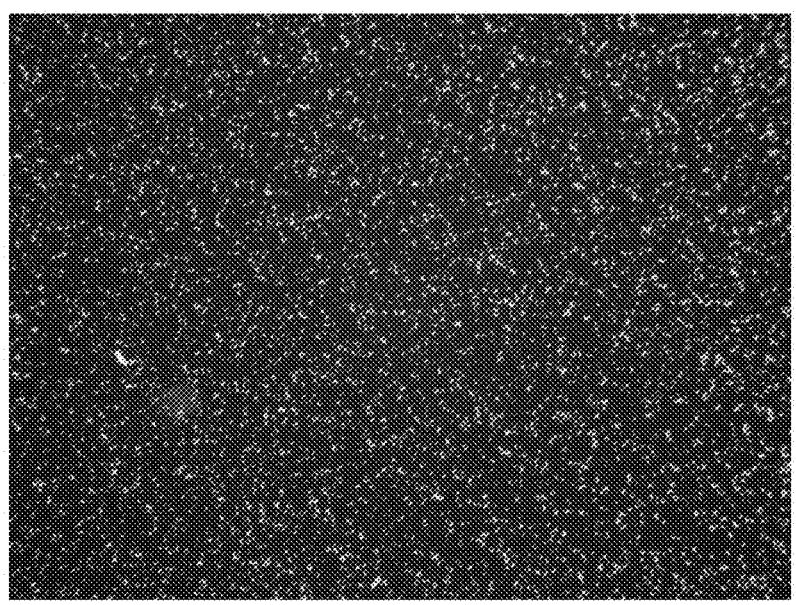
FIG. 4 shows Sample 20-3 roflumilast crystals suspended in equimolar hexylene glycol:water solution after storage for six weeks at room temperature under 4× power. The roflumilast crystals are 0.01 mm-0.02 mm in length.

0.0092 grams of roflumilast (Batch A14367P from Interquim S.A.) was weighed into a liquid scintillation vial. An equimolar blend of hexylene glycol (lot 1AC0818, Spectrum) and distilled water was added dropwise with mixing to the vial containing roflumilast to produce a suspension of roflumilast in excess of the solubility limit. An equimolar blend is 86.7% hexylene glycol and 13.3% water on a weight/weight percent basis. After mixing each addition of hexylene glycol:water blend, the tightly capped vial was returned to a water bath set at 25° C. It required 0.7962 grams of equimolar Hexylene Glycol:Water blend to completely dissolve the 0.0092 grams of roflumilast and give a 1.14% roflumilast in equimolar Hexylene Glycol:Water (wt/wt %) solution. 0.0064 grams of roflumilast was added to this sample (labeled 12-3) to form a finely dispersed suspension at 25° C. and the vial was then stored undisturbed at about 15-18° C., protected from the light for six weeks. A sample of the roflumilast crystals was removed from the vial, placed on a microscope slide (with coverslip) and then examined using polarized light microscopy using a 4× objective (FIG. 4, microscope sample 20-3).

Figure 5:
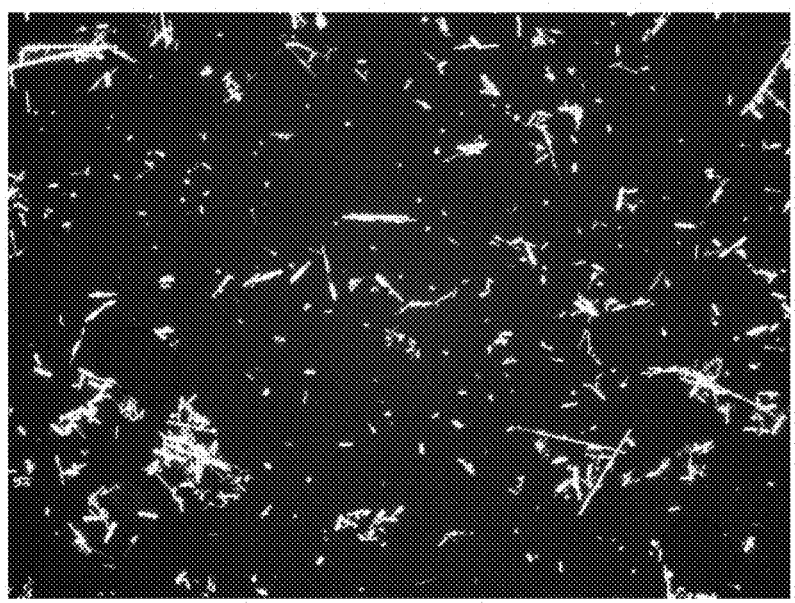
FIG. 5 shows Sample 21-2 roflumilast crystals suspended in equimolar ethanol:water solution after storage for six weeks at room temperature. The roflumilast crystals are 0.05 mm-0.25 mm in length and 0.02 mm in width.

0.0260 grams of roflumilast (Batch A14367P from Interquim S.A.) was weighed into a liquid scintillation vial. 1.0705 grams of an ethanol:water blend (Everclear which is 74.98% ethanol and 25.02% water on a weight/weight percent basis or 95% alcohol by volume) was added to produce a dispersion of roflumilast in an ethanol:water blend in excess of the solubility limit. This sample (labeled as "Alc" page 2) was then stored undisturbed at about 15-18° C., protected from the light for six weeks. A sample of the roflumilast crystals was removed from the vial, placed on a microscope slide (with coverslip) and then examined using polarized light microscopy using a 4× objective (FIG. 5, microscope sample 20-3).

Figure 6:
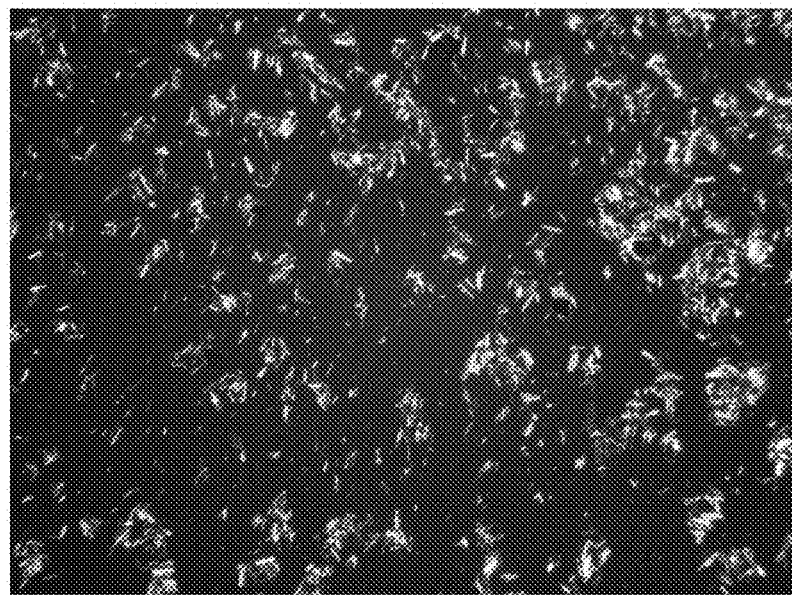
FIG. 6 shows Sample 21-3 roflumilast crystals suspended in equimolar PEG 400:water solution after storage for six weeks at room temperature. The roflumilast crystals are 0.05 mm-0.07 mm in length and 0.02 mm in width.

0.0180 grams of roflumilast (Batch A14367P from Interquim S.A.) was weighed into a liquid scintillation vial. Polyethylene glycol 400 (lot 1 DE0880, Spectrum) was added dropwise with mixing to the vial containing roflumilast to produce a suspension of roflumilast in excess of the solubility limit. After mixing each addition of polyethylene glycol 400, the tightly capped vial was returned to a water bath set at 25° C. It required 0.5486 grams of propylene glycol 400 to completely dissolve the 0.0180 grams of roflumilast and give a 3.18% roflumilast in polyethylene glycol 400 solution. This sample (labeled as "PEG 400" page 1) was a solution at 25° C. and was then stored undisturbed at about 15-18° C., protected from the light for six weeks. Roflumilast crystals precipitated due to the cooler storage temperature. A sample of the roflumilast crystals was removed from the vial, placed on a microscope slide (with coverslip) and then examined using polarized light microscopy using a 4× objective (FIG. 6, microscope sample 21-3).

Figure 7:
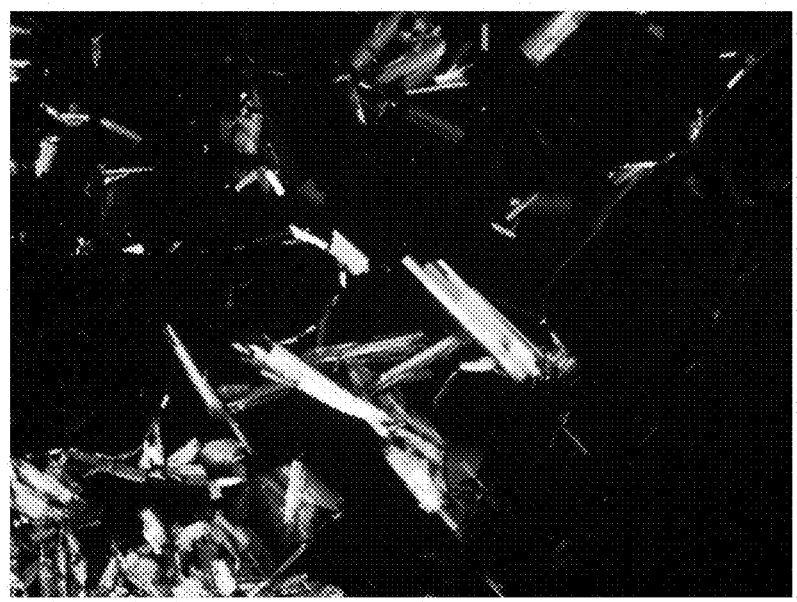
FIG. 7 shows Sample 21-4 roflumilast crystals suspended in equimolar DMSO:water solution after storage for six weeks at room temperature. The roflumilast crystals are 0.10 mm-0.67 mm in length and 0.02 mm-0.10 mm in width.

0.0103 grams of roflumilast (Batch A14367P from Interquim S.A.) was weighed into a liquid scintillation vial and mixed with 0.2501 grams of dimethyl sulfoxide (lot US150, Gaylord Chemical) to give a 28.5% solution of roflumilast at 25° C. This sample (labeled as "DMSO" page 2) was then stored undisturbed at about 15-18° C., protected from the light for six weeks. A sample of precipitated the roflumilast crystals was removed from the vial, placed on a microscope slide (with coverslip) and then examined using polarized light microscopy using a 4× objective (FIG. 7, microscope sample 21-4).

Figure 8:
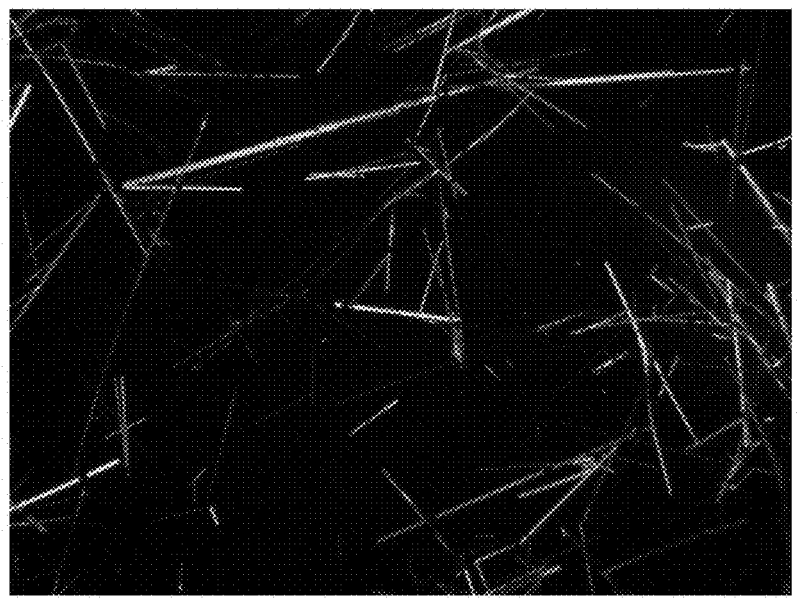
FIG. 8 shows Sample 21-5 roflumilast crystals suspended in equimolar propylene glycol:water solution after storage for six weeks at room temperature. The roflumilast crystals are 0.20 mm-1.60 mm in length and 0.02 mm in width.
Figure 9:
FIG. 9 shows Sample 20-1 roflumilast crystals suspended in equimolar NMP:water solution after storage for six weeks at room temperature. The roflumilast crystals are 0.10 mm-1.55 mm in length and 0.02 mm-0.13 mm in width.

0.0061 grams of roflumilast (Batch A14367P from Interquim S.A.), 1.9332 grams of propylene glycol (lot 1 EC0004, Spectrum) and 0.2335 grams distilled water was mixed to initially form a clear solution at 25° C. The composition of the sample was 0.28% roflumilast, 88.97% propylene glycol and 10.75% water on a weight/weight % basis. After 105 minutes of storage at 25° C. a "dusting" of fine roflumilast crystals were observed on the bottom of the vial. Six days later additional crystals had settled to the bottom of the vial. This sample (labeled 7-2) was then stored undisturbed at about 15-18° C., protected from the light for six weeks. A sample of precipitated roflumilast crystals was removed from the vial, placed on a microscope slide (with coverslip) and then examined using polarized light microscopy using a 4× objective (FIG. 8, microscope sample 21-5).

Example 3

Dramatically greater roflumilast crystalline growth was observed in an equimolar N-methyl pyrrolidone:water solution containing roflumilast in excess of drug saturation compared to a 12:4:3 (wt/wt/wt) blend of hexylene glycol: N-methyl pyrrolidone:water (1.2 mole fraction of water) solution having roflumilast added in excess of the solubility limit.

Figure 10:
FIG. 10 shows Sample 21-1 roflumilast crystals suspended in HG:NMP:Water (water mole fraction=1.2) solution after storage for six weeks at room temperature. The roflumilast crystals are 0.02 mm-0.04 mm in length and 0.02 mm in width.

0.0202 grams of roflumilast (Batch A14367P from Interquim S.A.) was mixed with 0.0682 grams of equimolar N-Methyl-2-pyrrolidone:water blend in a liquid scintillation vial. An equimolar blend is 84.5% N-Methyl-2-pyrrolidone (lot SYYN-HJ, TCI) and 15.5% water on a weight/weight percent basis. The 22.85% roflumilast in equimolar N-Methyl-2 pyrrolidone:water was completely dissolved at 25° C. This sample (labeled 13-2) was then stored undisturbed at about 15-18° C., protected from the light for six weeks. Roflumilast crystals precipitated due to the cooler storage temperature. A sample of the roflumilast crystals was removed from the vial, placed on a microscope slide (with coverslip) and then examined using polarized light microscopy using a 4× objective (FIG. 10, microscope sample 20-1).

Figure 11A:
FIGS. 11A and 11B show roflumilast particles precipitated in a cream composition after one freeze thaw cycle.
Figure 11B:
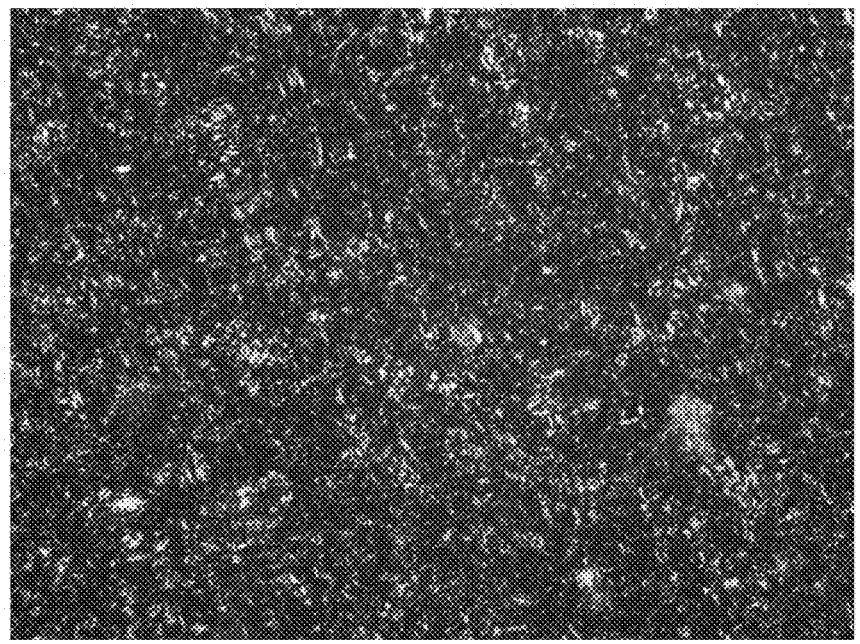

A 0.8152 gram sample of 3.6% roflumilast (Batch A14367P from Interquim S.A.), 60.8% hexylene glycol (lot 1AC0818, Spectrum), 20.0% N-Methyl-2-pyrrolidone (lot SYYN-HJ, TCI) and 15.6% distilled water was mixed on a weight/weight percent basis. This sample (labeled 13-4) was a finely dispersed suspension of roflumilast at 25° C. The sample was then stored undisturbed at about 15-18° C., protected from the light for six weeks. A sample of the roflumilast crystals was removed from the vial, placed on a microscope slide (with coverslip) and then examined using polarized light microscopy using a 4× objective (FIG. 11, microscope sample 21-1).

Example 4

Roflumilast creams were prepared according to the following formulations.

| Formulation 1 (comparative) | |
| --- | --- |
| Roflumilast | 0.5% w/w |
| White Petrolatum | 10.0% w/w |
| Isopropyl Palmitate | 5.0% w/w |
| Crodafos ™ CES (Cetearyl Alcohol, Dicetyl Phosphate, and Ceteth-10 Phosphate) | 10.0% w/w |
| Diethylene glycol monoethyl ether (Transcutol P) | 25% w/w |
| Methylparaben | 0.2% w/w |
| Propylparaben | 0.05% w/w |
| Purified Water | q.s. ad 100 (49.25%) |

| Formulation 2 | |
| --- | --- |
| Roflumilast | 0.5% w/w |
| White Petrolatum | 10.0% w/w |
| Isopropyl Palmitate | 5.0% w/w |
| Crodafos ™ CES (Cetearyl Alcohol, Dicetyl Phosphate, and Ceteth-10 Phosphate) | 10.0% w/w |
| Hexylene glycol | 2.0% w/w |
| Diethylene glycol monoethyl ether (Transcutol P) | 25.0% w/w |
| Methylparaben | 0.2% w/w |
| Propylparaben | 0.05% w/w |
| Purified Water | q.s. ad 100 (47.25%) |

After preparation, 0.4222 grams of formulation 1 was sealed in a 1.0 mL CryoTube™ vial and labeled as 36-1. Likewise, 0.3961 grams of formulation 2 was sealed in a 1.0 mL CryoTube™ vial and labeled as 36-2. The two Cryo-Tube™ vials were secured in an envelope end-to-end and placed in the freezer for 17.5 hours. Quickly upon removal from the freezer, a microscopic slide was prepared of each sample and after "thawing" the sample to room temperature (18° C.) a photomicrograph images was captured to characterize differences in precipitated roflumilast crystal growth. See FIGS. 11A and 11B.

The invention claimed is:

1. A method for inhibiting roflumilast crystal growth or changes in particle size in a composition, comprising including hexylene glycol in a composition comprising roflumilast.

2. The method according to claim 1, wherein said composition comprises suspended roflumilast particles.

3. The method according to claim 2, wherein changes in the size of the suspended roflumilast particles is inhibited during storage for six weeks at 20-26° C.

4. The method according to claim 1, wherein said hexylene glycol is added in an amount of 0.1-20% w/w.

5. The method according to claim 4, wherein said hexylene glycol is added in an amount of 0.5-2% w/w.

6. The method according to claim 1, wherein said roflumilast composition comprises 0.005-2% roflumilast.

7. The method according to claim 1, wherein said roflumilast composition is selected from the group consisting of an oil in water emulsion, a thickened aqueous gel, a thickened hydroalcoholic gel, a hydrophilic gel, and a hydrophilic or hydrophobic ointment.

8. The method according to claim 1, wherein said roflumilast composition further comprises at least one additional component selected from the group consisting of a solvent, moisturizer, surfactant or emulsifier, polymer or thickener, antifoaming agent, preservative, antioxidant, sequestering agent, stabilizer, buffer, pH adjusting solution, skin penetration enhancer, film former, dye, pigment, and fragrance.

9. The method according to claim 1, wherein said roflumilast composition further comprises an additional active agent selected from the group consisting of anthralin, azathioprine, tacrolimus, coal tar, methotrexate, methoxsalen, salicylic acid, ammonium lactate, urea, hydroxyurea, 5-fluorouracil, propylthouracil, 6-thioguanine, sulfasalazine, mycophenolate mofetil, fumaric acid esters, corticosteroids, corticotropin, vitamin D analogues, acitretin, tazarotene, cyclosporine, resorcinol, colchicine, adalimumab, ustekinumab, infliximab, bronchodialators, and antibiotics.

10. The method according to claim 1 wherein said hexylene glycol is added to said composition prior to storage.

11. The method according to claim 1, wherein said composition comprises one or more carriers suitable for topical, parenteral or pulmonary administration.

12. The method according to claim 1, wherein said composition comprises one or more carriers suitable for topical administration.

13. The method according to claim 1, further comprising adding diethylene glycol monoethyl ether to said composition.

14. The method according to claim 1, wherein said composition comprises roflumilast, white petrolatum, isopropyl palmitate, cetearyl alcohol, dicetyl phosphate, ceteth-10 phosphate, hexylene glycol, diethylene glycol monoethyl ether, methylparaben, propylparaben, and purified water.

15. The method according to claim 14, wherein the composition comprises:

| | |
|---|---|
| roflumilast | 0.5% w/w |
| white petrolatum | 10.0% w/w |
| isopropyl palmitate | 5.0% w/w |
| cetearyl alcohol, dicetyl phosphate, and ceteth-10 phosphate | 10.0% w/w |
| hexylene glycol | 2.0% w/w |
| diethylene glycol monoethyl ether | 25.0% w/w |
| methylparaben | 0.2% w/w |
| propylparaben | 0.05% w/w, and |
| purified water | q.s. ad 100 (47.25%). |

16. The method according to claim 4, wherein said hexylene glycol is added in an amount of 0.25-8% w/w.

* * * * *